United States Patent [19]

Caufield

[11] Patent Number: 5,118,677
[45] Date of Patent: Jun. 2, 1992

[54] AMIDE ESTERS OF RAPAMYCIN
[75] Inventor: Craig E. Caufield, Plainsboro, N.J.
[73] Assignee: American Home Products Corporation, New York, N.Y.
[21] Appl. No.: 703,240
[22] Filed: May 20, 1991
[51] Int. Cl.[5] .................. A61K 31/395; C07D 491/06
[52] U.S. Cl. .................. 514/183; 514/321; 540/456
[58] Field of Search .................. 540/456; 514/183, 321

[56] References Cited

U.S. PATENT DOCUMENTS

| | | | |
|---|---|---|---|
| 3,929,992 | 12/1975 | Seghah et al. | 424/122 |
| 3,993,749 | 11/1976 | Seghal et al. | 424/122 |
| 4,316,885 | 2/1982 | Rakhit | 424/122 |
| 4,401,653 | 8/1983 | Eng | 424/114 |
| 4,885,171 | 12/1989 | Surendra et al. | 424/122 |

OTHER PUBLICATIONS

J. Antibiot. 28, 721-726 (1975).
J. Antibiot. 28, 727-732 (1975).
J. Antibiot. 31, 539-545 (1978).
Can. J. Physiol. Pharmacol. 55, 48(1977).
FASEB 3,3411 (1989).
FASEB 3,5256 (1989).
Lancet 1183 (1978).
Med. Sci Res. 17:877 (1989).

Primary Examiner—Robert T. Bond
Attorney, Agent, or Firm—Arnold S. Milowsky

[57] ABSTRACT

A compound of the structure

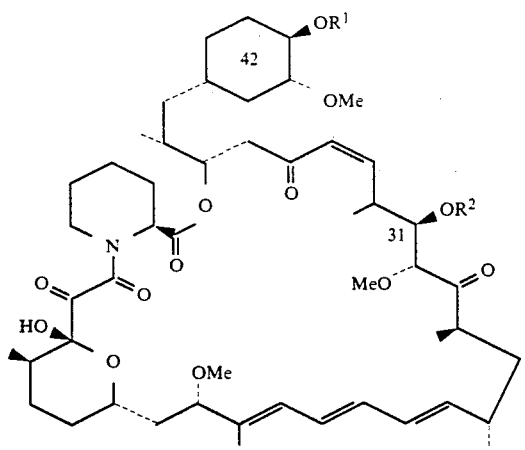

wherein $R^1$ and $R^2$ are each independently, hydrogen or

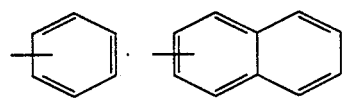

X is —$(CH_2)_m$— or —Ar—; $R^3$ and $R^4$ are each, independently, hydrogen, alkyl, —$(CH_2)_n$—Ar, —$(CH_2)_p$—$NR^5R^6$, or —$(CH_2)_p$—$N^+R^5R^6R^7Y^-$; $R^5$ and $R^6$ are each, independently, hydrogen, alkyl, or —$(CH_2)_n$—Ar; Ar is an optionally substituted group selected from

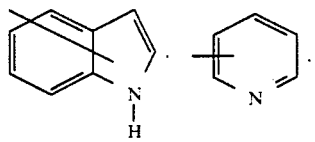

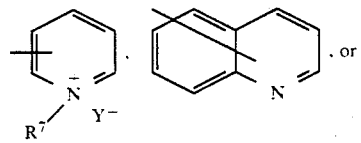 , or

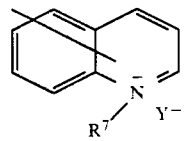

in which the optional substituents are selected from the group consisting of alkyl, aralkyl, alkoxy, cyano, halo, nitro, carbalkoxy, or perfluoroalkyl; $R^7$ is alkyl; Y is a halide, sulfate, phosphate, or p-toluenesulfonate anion; m=1-6; n=1-6; p=1-6; with the proviso that $R^1$ and $R^2$ are not both hydrogen; or a pharmaceutically acceptable salt thereof, which by virtue of its immunosuppressive activity is useful in treating transplantation rejection, host vs. graft disease, autoimmune diseases and diseases of inflammation; by virtue of its antitumor activity is useful in treating solid tumors; and by virtue of its antifungal activity is useful in treating fungal infections.

10 Claims, No Drawings 5,118,677

AMIDE ESTERS OF RAPAMYCIN

BACKGROUND OF THE INVENTION

This invention relates to amide esters of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions.

DESCRIPTION OF THE INVENTION

This invention provides derivatives of rapamycin which are useful as immunosuppressive, anti-inflammatory, antifungal, and antitumor agents having the structure

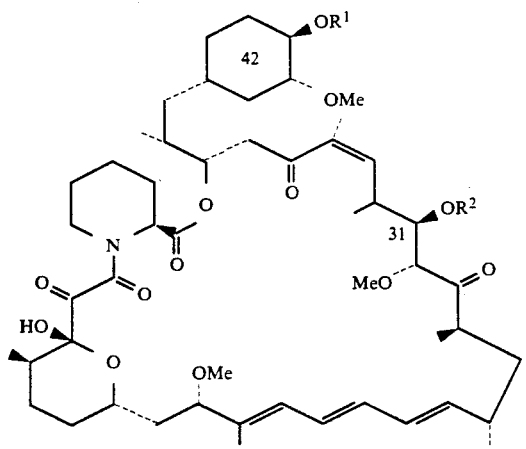

wherein
$R^1$ and $R^2$ are each independently, hydrogen or

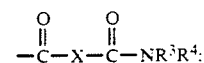

X is $-(CH_2)_m-$ or $-Ar-$;
$R^3$ and $R^4$ are each, independently, hydrogen, alkyl of 1-12 carbon atoms, $-(CH_2)_n-Ar$, $-(CH_2)_p-NR^5R^6$, or $-(CH_2)_p-N^+R^5R^6R^7Y^-$;
$R^5$ and $R^6$ are each, independently, hydrogen, alkyl of 1-12 carbon atoms, or $-(CH_2)_n-Ar$;
Ar is an optionally mono- or di- substituted group selected from

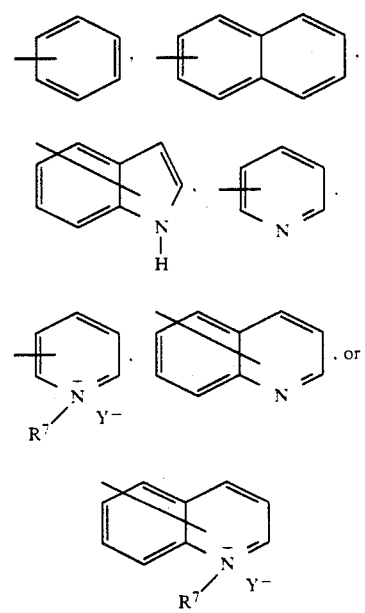

in which the optional substituents are selected from the group consisting of alkyl of 1-6 carbon atoms, aralkyl of 7-10 carbon atoms, alkoxy of 1-6 carbon atoms, cyano, halo, nitro, carbalkoxy of 2-7 carbon atoms, or perfluoroalkyl of 1-6 carbon atoms;
$R^7$ is alkyl of 1-6 carbon atoms;
Y is a halide, sulfate, phosphate, or p-toluenesulfonate anion;
m = 1-6;
n = 1-6;
p = 1-6;
with the proviso that $R^1$ and $R^2$ are not both hydrogen;
or a pharmaceutically acceptable salt thereof.

Pharmaceutically acceptable salts may be formed when $R^3$ or $R^4$ is $-(CH2)p-NR^5R^6$ or when Ar is an optionally mono- or di- substituted pyridyl or quinolyl group. The pharmaceutically acceptable salts are derived from such organic and inorganic acids such as, acetic, lactic, citric, tartaric, succinic, maleic, malonic, gluconic, hydrochloric, hydrobromic, phosphoric, nitric, sulfuric, methanesulfonic, and the like.

Of these compounds, preferred members are those in which X is $-(CH_2)_m-$; those in which X is $-(CH_2)_m-$ and $R^3$ and $R^4$ are alkyl of 1-6 carbon atoms; and those in which X is $-(CH_2)_m-$, $R^3$ is hydrogen, and $R^4$ is and Ar is $-(CH_2)_n-Ar$.

The compounds of this invention acylated at the 42-position can be prepared by acylating rapamycin with an amido-acid acylating agent having the general structure

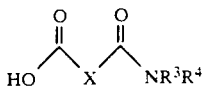

in the presence of a coupling reagent, such as a suitably substituted carbodiimide coupling reagent.

The compounds of this invention acylated at both the 31- and 42-positions can be prepared by the method described above by increasing variables such as reaction time, temperature, and quantity of acylating agent.

The 31-acylated compounds of this invention can be prepared by protecting the 42-alcohol of rapamycin with a protecting group, such as with a tert-butyl dimethylsilyl group in the presence of a base, such as imidazole, followed by acylation of the 31-position with an acylating agent having the general structure shown above. Removal of the protecting group provides the 31-acylated compounds. In the case of the tert-butyl dimethylsilyl protecting group, deprotection can be accomplished under mildly acidic conditions, such as with a mixture of aqueous acetic acid and THF.

Having the 31-position acylated and the 42-position deprotected, the 42-position can be reacted with a different amido-acid of the generic structure described above than was reacted with the 31-alcohol, to give compounds having different acyl moieties at the 31- and 42-positions. Alternatively, the 42-acyl compounds, prepared as described above, can be reacted with an acylating agent having a different structure to provide compounds having different acyl moieties at the 31-and 42-positions.

The acylating groups used to prepare the compounds of the invention are can be prepared by the method outlined below from anhydrides that are either commercially available or by methods that are that are disclosed in the literature.

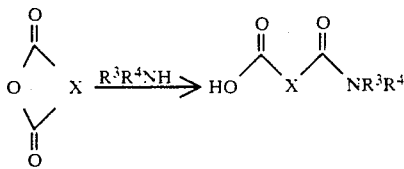

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. The results are expressed by the following ratio.

$$\frac{{}^3\text{H-control thymus cells} - {}^3\text{H-rapamycin-treated thymus cells}}{{}^3\text{H-control thymus cells} - {}^3\text{H-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg. p.o. gave 86% suppression, whereas cyclosporin A at the same dose gave 43% suppression. Results are expressed by the following ratio:

$$\frac{{}^3\text{H-PLN cells control C3H mouse} - {}^3\text{H-PLN cells rapamycin-treated C3H mouse}}{{}^3\text{H-PLN cells control C3H mouse} - {}^3\text{H-PLN cells test compound-treated cells}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S. D.) of the drug treatment group is compared with the control group.

The following table summarizes the results of representative compounds of this invention in these three standard test procedures.

TABLE 1

| Compound | LAF (ratio) | PLN (ratio) | Skin Graft (days + SD) |
|---|---|---|---|
| Example 1 | 1.94 | 0.62 | + |
| Example 2 | 0.14 | + | + |
| Example 3 | 0.19 | 0.76 | 7.5 ± 1.5 |
| Example 4 | 0.91 | 0.59 | 9.5 ± 0.8 |
| Rapamycin | 1.00 | 1.00 | 12.0 ± 1.7 |

+ Not evaluated.

The results of these standard pharmacological test procedures demonstrate immunosuppressive activity both in vitro and in vivo for the compounds of this invention. Positive ratios in the LAF and PLN test procedures indicate suppression of T cell proliferation. As a transplanted pinch skin grafts are typically rejected within 6-7 days without the use of an immunosuppressive agent, the increased survival time of the skin graft when treated with the compounds of this invention further demonstrates their utility as immunosuppressive agents.

Because the compounds of this invention are structurally similar to rapamycin and have a similar activity profile to rapamycin, the compounds of this invention also are considered to have antitumor and antifungal activities.

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease, and eye uveitis; solid tumors; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1-5 percent, preferably 2%, of active compound which may be administered to a fungally affected area.

The following examples illustrate the preparation of representative compounds of this invention.

EXAMPLE 1

Rapamycin 42-ester with 4-(dimethylamino)-4-oxobutanoic acid

To a solution of 1.00 g (1.09 mmol) of rapamycin in 20 mL of dry dichloromethane was added 316 mg (2.18 mmol) of N,N-dimethylsuccinamic acid, 15 mg of 4-N,N-dimethylaminopyridine followed by 476 mg (mmol) of 1-(3-dimethylaminopropyl)-3-ethylcarbodiimide hydrochloride. The solution was stirred overnight and then poured into 1N HCl and extracted three times with ethyl acetate. The organic layers were combined, washed with brine, dried over anhydrous sodium sulfate, filtered, and concentrated in vacuo to give a pale yellow foamy solid. The residue was flash chromatographed on a 40 mm × 150 mm silica column eluting with 40-60% ethyl acetate/hexane to give 105 mg (10%) of pure rapamycin 42-ester with 4-(dimethylamino)-4-oxobutanoic acid, which was isolated as the monohydrate. The spectral data follows: $^1$H NMR (CDCl$_3$, 400 MHz) δ 4.81 (s, 1 H, anomeric OH), 4.66 (m, 1 H, —CHO$_2$CCH$_2$), 4.19 (m, 1 H, 31—CHOH), 3.39 (s, 3 H, —OCH$_3$), 3.33 (s, 3 H, —OCH$_3$), 3.14 (s, 3 H, —OCH$_3$), 3.03 (s, 3 H, —CONCH$_3$), 2.95 (s, 3 H, —CONCH$_3$), 2.67 (m, 4 H, —O$_2$CCH$_2$CH$_2$CONMe$_2$), 1.75 (s, 3 H, CH$_3$C=C—), 1.65 (s, 3 H, CH$_3$C=C—); IR (KBr) 3450 (OH), 2940, 2890, 1735 (C=O), 1650 (C=O), 1455, 1380, 1295, 1105, 995 cm$^{-1}$; MS (neg. ion FAB) 1040 (M-); MS Peak Matching (neg. ion FAB) calcd for 1040.61842, found 1040.6196.

Analysis Calcd for C$_{57}$H$_{88}$N$_2$O$_{15}$: C 65.74; H 8.52; N 2.69; Found: C 65.81; H 8.73; N 2.42.

The following representative compounds can be prepared from rapamycin and the appropriate amido-ester by employing the method used to prepare the title compound in Example 1.

Rapamycin-42-ester with 4-[[1-(4-chlorophenyl)methyl]amino]-4-oxobutanoic acid

Rapamycin-42-ester with 5-[[3-(2-naphthyl)propyl]amino]-5-oxopentanoic acid

Rapamycin-42-ester with 6-(N-methyl-N-hexylamino)-6-oxohexanoic acid

Rapamycin-42-ester with 4-[[3-(dimethylamino)propyl]amino]-4-oxobutanoic acid

Rapamycin-42-ester with 5-[[4-(octylamino)butyl]amino]-5-oxopentanoic acid

Rapamycin-42-ester with 4-[[2-(3-(6-hydroxyquinolyl))ethyl]amino]-4-oxobutanoic acid Rapamycin-42-ester with 4-[[2-(phenylmethylamino)ethyl]amino]-4-oxobutanoic acid Rapamycin-42-ester with 5-(N-hexyl-N-decylamino)-5-oxopentanoic acid Rapamycin-42-ester with 2-(dimethylcarbamyl) benzoic acid Rapamycin-42-ester with 2-[[3-(diethylamino)propyl]carbamyl] benzoic acid Rapamycin-42-ester with 2-[(phenylmethyl)carbamyl] nicotinic acid Rapamycin-42-ester with 3-[(phenylmethyl)carbamyl] picolinic acid Rapamycin-31,42-diester with 4-[[1-(4-chlorophenyl)methyl]amino]-4-oxobutanoic acid Rapamycin-31,42-diester with 6-(N-methyl-N-hexylamino)-6-oxohexanoic acid Rapamycin-31,42-diester with 4-[[3-(dimethylamino)propyl]amino]-4-oxobutanoic acid Rapamycin-31,42-diester with 5-[[4-(octylamino)butyl]amino]-5-oxopentanoic acid Rapamycin-31,42-diester with 4-[[2-(3-(6-hydroxyquinolyl))ethyl]amino]-4-oxobutanoic acid Rapamycin-31,42-diester with 4-[[2-(phenylmethylamino)ethyl]amino]-4-oxobutanoic acid Rapamycin-31,42-diester with 4-[[2-(2-indolyl)ethyl]amino]-4-oxobutanoic acid Rapamycin-31,42-diester with 5-(N-hexyl-N-decylamino)-5-oxopentanoic acid Rapamycin-31,42-diester with 2-(dimethylcarbamyl)benzoic acid Rapamycin-31,42-diester with 2-[[3-(diethylamino)propyl]carbamyl]benzoic acid

EXAMPLE 2

Rapamycin 31,42-diester with 4-oxo-4-[[2-(2-pyridinyl)ethyl]amino]butanoic acid

To a solution of 5.0 g (50 mmol) of succinic anhydride in 50 mL of dichloromethane was added 550 mg of DMAP and 6.1 g (50 mmol) of 2-(2'-aminoethyl)pyridine. An exothermic reaction resulted. The reaction was refluxed for 1 h and cooled to room temperature and stirred for 48 h. The reaction is worked up by concentrated in vacuo; the resulting solid was dissolved in pH 4 buffer and extracted three times with 4:1 ethyl acetate/tetrahydrofuran after the aqueous solution had been saturated with ammonium sulfate. The organic layer was dried over sodium sulfate and concentrated in vacuo to give a residue. The residue was recrystallized from ethyl acetate/methanol to give 5.5 g (50%) of 4-oxo-4-[[2-(2-pyridinyl)ethyl]amino]butanoic acid.

To a solution of 3.8 g (4.19 mmol) of rapamycin in 125 mL of dichloromethane was added at room temperature, 200 mg of DMAP, 4.3 g (20.9 mmol) of dicyclohexyl-carbodiimide and 4.6 g (20.7 mmol) of 4-oxo-4-[[2-(2-pyridinyl)ethyl]amino]butanoic acid. The reaction was stirred overnight at room temperature. The reaction mixture was poured into water and extracted twice with ethyl acetate. The combined organic extracts were dried over sodium sulfate and concentrated in vacuo to give a solid residue. The residue was purified by preparative HPLC (Waters Prep 500, 5% methanol/ethyl acetate) to give 4.30 g (79%) of pure rapamycin 31,42-ester with 4-oxo-4-[[2-(2-pyridinyl)-ethyl]amino]butanoic acid.

The spectral data follows: $^1$H NMR (CDCl$_3$, 400 MHz) $\delta$8.53 (s, 1 H, arom), 7.67 (m, 1 H, arom), 7.22 (m, 2 H, arom), 6.74 (m, 1 H, arom), 4.63 (m, 1 H, —CHO$_2$CCH$_2$), 4.18 (m, 1 H, 31—CHOH), 3.68 (m, 2 H, —CONHCH$_2$), 3.36 (s, 3 H, —OCH$_3$), 3.35 (s, 3 H, —OCH$_3$), 3.14 (s, 3 H, —OCH$_3$), 3.02 (m, 2 H, CH$_2$Pyr), 2.67 (s, 3 H, —O$_2$CCH$_2$CH$_2$CONHR), 1.75 (s, 3 H, CH$_3$C=C—), 1.66 (s, 3 H, CH$_3$C=C—); IR (KBr) 3390 (OH), 2930, 2850, 1735 (C=O), 1640 (C=O), 1535, 1455, 1380, 1295, 1100, 995 cm$^{-1}$; MS (neg. FAB) 1321 (M-).

The following representative compounds can be prepared from rapamycin and the appropriate amido-ester by employing the method used to prepare the title compound in Example 2.

EXAMPLE 3

Rapamycin 31,42-diester with 4-oxo-4-[[2-(2-pyridinyl)ethyl]amino]butanoic acid dihydrochloride To a solution of 500 mg (378 μmol) of rapamycin 31,42-ester with 4-oxo-4-[[2-(2-pyridinyl)ethyl]amino]butanoic acid in 2 mL of methanol was added 56 μL of acetyl chloride. The reaction mixture is concentrated in vacuo to give 530 mg (100%) of pure rapamycin 31,42-ester with 4-oxo-4-[[2-(2-pyridinyl)ethyl]amino]butanoic acid dihydrochloride.

The spectral data follows: $^1$H NMR (d$_6$-DMSO, 400 MHz) $\delta$ 8.53 (s, 1 H, arom), 8.32 (m, 1 H, arom), 7.76 (m, 2 H, arom), 8.06 (m, 1 H, arom), 3.45 (m, 5 H, —OCH$_3$ and —CONHCH$_2$), 3.44 (s, 3 H, —OCH$_3$), 3.23 (s, 3 H, —OCH$_3$), 3.07 (m, 2 H, CH$_2$Pyr), 2.49 (s, 3 H, —O$_2$CCH$_2$CH$_2$CONHR), 1.79 (s, 3 H, CH$_3$C=C—), 1.66 (s, 3 H, CH$_3$C=C—); IR (KBr) 3400 (OH), 2920, 2850, 1735 (C=O), 1635 (C=O), 1545, 1440, 1370, 1150, 985 cm$^{-1}$; MS (neg. FAB) calculated for C$_{73}$H$_{113}$N$_5$O$_{17}$ 1321.8950, found 1321.7350; MS (neg. FAB) 1321 (free base, M-), 590, 446 (100), 297.

Analysis Calcd for C$_{73}$H$_{115}$N$_5$O$_{17}$Cl$_2$.5 H$_2$O: C 56.04; H 6.71; N 4.47; Found: C 55.66; H 6.36; N 4.29.

EXAMPLE 4

Rapamycin 31,42-diester with 2-[2-[(3-carboxyl-1-oxopropyl)amino]ethyl]-1-methylpyridinium iodide To a solution of 500 mg (378 μmol) of rapamycin 31,42-ester with 4-oxo-4-[[2(2-pyridinyl)ethyl]amino]butanoic acid in 2 mL of acetone was added 50 μL of methyl iodide and the reaction was stirred overnight at room temperature. The reaction was incomplete so 25 μL of methyl iodide was added and refluxed. The reaction mixture was cooled to room temperature and concentrated in vacuo to give 580 mg (98%) of rapamycin 31,42-ester with 2-[2-[(3-carboxy-1-oxopropyl)amino]ethyl]-1-methylpyridinium iodide, which was isolated as the tetrahydrate.

The spectral data follows: $^1$H NMR (CDCl$_3$, 400 MHz) $\delta$ 9.05 (m, 1 H, arom), 8.40 (m, 1 H, arom), 8.04 (m, 1 H, arom), 7.89 (m, 2 H, arom), 4.53 (s, 3 H, NCH$_3$+), 3.64 (m, 2 H, —CONHCH$_2$), 3.38 (s, 3 H, —OCH$_3$), 3.33 (s, 3 H, —OCH$_3$), 3.12 (s, 3H, —OCH$_3$), 3.09 (m, 2 H, CH$_2$Pyr), 2.56 (s, 3 H, —O$_2$CCH$_2$CH- $_2$CONHR), 1.82 (s, 3 H, CH$_3$C=C—), 1.64 (s, 3 H, CH$_3$C=C—); IR (KBr) 3410 (OH), 2920, 2840, 1720 (C=O), 1625 (C=O), 1535, 1430, 1360, 1225, 1100, 985 cm$^{-1}$; MS (neg. FAB) 1605 (M-).

Analysis Calcd for C$_{75}$H$_{109}$N$_5$O$_{17}$I$_2$. 4 H$_2$O: C 53.67; H 6.97; N 4.17; Found: C 53.96; H 6.83; N 3.72.

The following representative compounds can be prepared from an appropriately substituted rapamycin ester and an appropriately substituted alkylating agent by employing the method used to prepare the title compound in Example 4.

Rapamycin-31,42-diester with 3-[(3-carboxy-1-oxopropyl)amino]propyl trimethyl ammonium iodide Rapamycin-31,42-diester with 3-[(3-carboxy-1-oxopropyl)amino]propyl trimethyl ammonium sulfate Rapamycin-31,42-diester with 3-[(3-carboxy-1-oxopropyl)amino]propyl trimethyl ammonium phosphate Rapamycin-31,42-diester with 3-[(3-carboxy-1-oxopropyl)amino]propyl trimethyl ammonium p-toluenesulfonate Rapamycin-31,42-diester with 3-[2-[(3-carboxy-1-oxopropyl)amino]ethyl]-1-methylquinolinium iodide

What is claimed is:

1. A compound of the formula

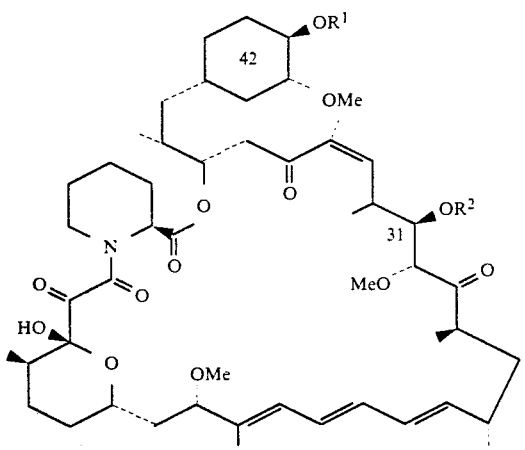

wherein
R$^1$ and R$^2$ are each independently, hydrogen or

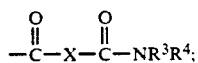

X is —(CH$_2$)$_m$— or —Ar—;
R$^3$ and R$^4$ are each, independently, hydrogen, alkyl of 1-12 carbon atoms, —(CH$_2$)$_n$—Ar, —(CH$_2$)$_p$—NR$^5$R$^6$, or —(CH$_2$)$_p$—N$^+$R$^5$R$^6$R$^7$Y$^-$;
R$^5$ and R$^6$ are each, independently, hydrogen, alkyl of 1-12 carbon atoms, or —(CH$_2$)$_n$—Ar;
Ar is an optionally mono- or di- substituted group selected from

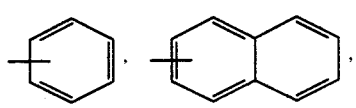

-continued

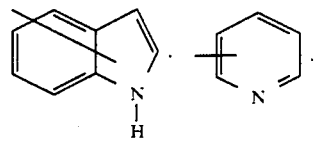

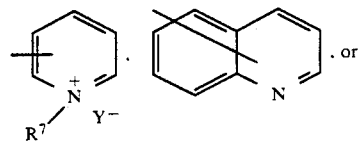

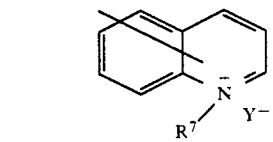

in which the optional substituents are selected from the group consisting of alkyl of 1-6 carbon atoms, phenylalkyl of 7-10 carbon atoms, alkoxy of 1-6 carbon atoms, cyano, halo, nitro, carbalkoxy of 2-7 carbon atoms, or perfluoroalkyl of 1-6 carbon atoms;

R$^7$ is alkyl of 1-6 carbon atoms;
Y is a halide, sulfate, phosphate, or p-toluenesulfonate anion;
m=1-6;
n=1-6;
p=1-6;
with the proviso that R$^1$ and R$^2$ are not both hydrogen;

or a pharmaceutically acceptable salt thereof.

2. A compound according to claim 1 in which X is —(CH$_2$)$_m$—.

3. A compound according to claim 1 in which X is —(CH$_2$ $_2$)$_m$— and R$^3$ and R$^4$ are alkyl of 1-6 carbon atoms.

4. A compound according to claim 1 in which X is —(CH$_2$)$_m$—, R$^3$ is hydrogen, and R$^4$ is and Ar is —(CH$_2$)$_n$—Ar.

5. A compound according to claim 1 which is rapamycin 42-ester with 4-(dimethylamino)-4-oxobutanoic acid.

6. A compound according to claim 1 which is rapamycin 31,42-diester with 4-oxo-4-[[2-(2-pyridinyl)ethyl]amino]butanoic acid or a pharmaceutically acceptable salt thereof.

7. A compound according to claim 6 which is rapamycin 31,42-diester with 4-oxo-4-[[2-(2-pyridinyl)ethyl]amino]butanoic acid dihydrochloride.

8. A compound according to claim 1 which is rapamycin 31,42-diester with 2-[2-[(3-carboxy-1oxopropyl)amino]ethyl]-1-methyl-pyridinium iodide.

9. A method of treating transplantation rejection, host vs. draft disease, autoimmune diseases, and diseases of inflammation in a mammal by administering an effective amount of a compound having the formula

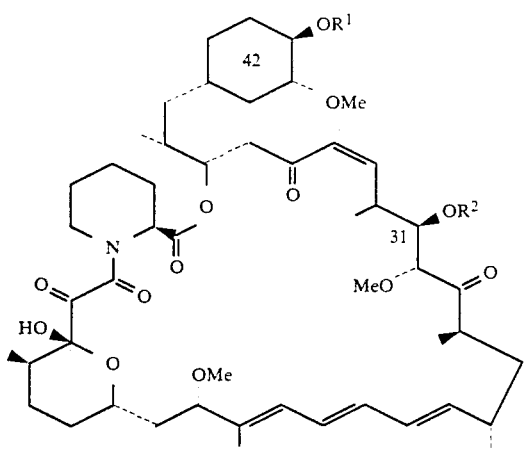

wherein
R¹ and R² are each independently, hydrogen or

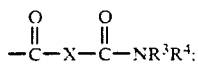

X is —(CH₂)$_m$— or —Ar—;
R³ and R⁴ are each, independently, hydrogen, alkyl of 1–12 carbon atoms, —(CH₂)$_n$—Ar, —(CH₂)$_p$—NR⁵R⁶, or —(CH₂)$_p$—N⁺R⁵R⁶R⁷Y⁻;
R⁵ and R⁶ are each, independently, hydrogen, alkyl of 1–12 carbon atoms, or —(CH₂)$_n$—Ar;
Ar is an optionally mono- or di- substituted group selected from

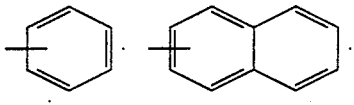

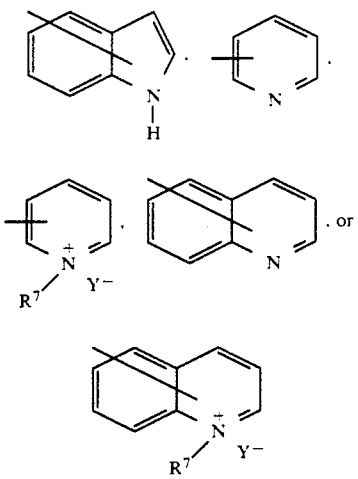

in which the optional substituents are selected from the group consisting of alkyl of 1–6 carbon atoms phenylalkyl of 7–10 carbon atoms, alkoxy of 1–6 carbon atoms, cyano, halo, nitro, carbalkoxy of 2–7 carbon atoms, or perfluoroalkyl of 1–6 carbon atoms;
R⁷ is alkyl of 1–6 carbon atoms;
Y is a halide, sulfate, phosphate, or p-toluenesulfonate anion;
m = 1–6;
n = 1–6;
p = 1–6;
with the proviso that R¹ and R² are not both hydrogen;
or a pharmaceutically acceptable salt thereof.

10. A pharmaceutical composition for use as an immunosuppressive agent comprising an immunosuppressive amount of a compound of claim 1 and a pharmaceutical carrier.

* * * * *